US010362784B2

(12) United States Patent
Sanford et al.

(10) Patent No.: US 10,362,784 B2
(45) Date of Patent: Jul. 30, 2019

(54) COMPOSITIONS AND METHODS FOR FORMING STABLE, LIQUID METAL OXIDE/HYDROXIDE FORMULATIONS

(71) Applicant: Timilon Technology Acquisitions LLC, Fort Meyers, FL (US)

(72) Inventors: Bill Sanford, Naples, FL (US); Brandon Walker, Wamego, KS (US); Paul S. Malchesky, Painesville, OH (US); Kyle Knappenberger, Topeka, KS (US); Calvin Jeffrey Kissick, Lawrence, KS (US); Eric Steward, Manhattan, KS (US)

(73) Assignee: Timilon Technology Acquisitions LLC, Fort Meyers, FL (US)

( * ) Notice: Subject to any disclaimer, the term of this patent is extended or adjusted under 35 U.S.C. 154(b) by 0 days.

(21) Appl. No.: 15/639,717

(22) Filed: Jun. 30, 2017

(65) Prior Publication Data
US 2018/0007914 A1 Jan. 11, 2018

Related U.S. Application Data

(60) Provisional application No. 62/358,365, filed on Jul. 5, 2016.

(51) Int. Cl.
A01N 59/06 (2006.01)
A01N 59/00 (2006.01)
A61Q 17/00 (2006.01)
A61Q 19/10 (2006.01)
A61K 8/34 (2006.01)
A61K 8/19 (2006.01)
A61K 8/27 (2006.01)
A61K 8/29 (2006.01)
(Continued)

(52) U.S. Cl.
CPC ............ A01N 59/06 (2013.01); A01N 25/10 (2013.01); A01N 25/22 (2013.01); A01N 25/30 (2013.01); A01N 59/00 (2013.01); A61K 8/022 (2013.01); A61K 8/04 (2013.01); A61K 8/06 (2013.01); A61K 8/19 (2013.01); A61K 8/27 (2013.01); A61K 8/29 (2013.01); A61K 8/345 (2013.01); A61K 8/39 (2013.01); A61K 8/466 (2013.01); A61K 8/4993 (2013.01); A61K 8/8152 (2013.01); A61K 8/88 (2013.01); A61K 8/90 (2013.01); A61Q 17/005 (2013.01); A61Q 19/10 (2013.01); C09D 1/00 (2013.01); C09D 5/031 (2013.01); C09D 5/036 (2013.01); C09D 5/14 (2013.01); C09D 7/45 (2018.01); C09D 7/61 (2018.01); C09D 7/62 (2018.01); C09D 7/63 (2018.01); C09D 7/65 (2018.01); C09D 201/00 (2013.01); C11D 1/008 (2013.01); C11D 1/146 (2013.01); C11D 1/667 (2013.01); C11D 1/72 (2013.01); C11D 1/74 (2013.01); C11D 1/831 (2013.01); C11D 3/0068 (2013.01); C11D 3/1213 (2013.01); C11D 3/2065 (2013.01); C11D 3/3707 (2013.01); C11D 3/3719 (2013.01); C11D 3/3761 (2013.01); C11D 3/382 (2013.01); C11D 3/43 (2013.01); C11D 3/48 (2013.01); C11D 17/0013 (2013.01); C11D 17/06 (2013.01); A61K 2800/413 (2013.01); C08K 3/22 (2013.01)

(58) Field of Classification Search
CPC ........ A01N 59/06; A01N 25/06; A01N 59/00; A01N 59/16; A01N 59/20; A01N 25/16; A01N 25/04; A01N 25/34; A61K 2300/00; A61K 36/00; A61K 36/31; A61K 36/185; A61K 36/23; A61K 36/28; A61K 36/286; A61K 36/42; A61K 36/47; A61K 36/48; A61K 36/889; A61K 36/899; A61K 31/167; A61K 31/185; A61K 31/403; A61K 31/436; A61K 31/551; A61K 31/5513; A61K 47/20; A61K 47/44; A61K 8/06; A61K 8/66; A61K 8/922; A61K 9/0014; A61K 9/5047; A61K 9/5078; A61K 2039/507; A61K 2039/54; A61K 2039/55566; A61K 2039/55588; A61K 2800/413; A61K 39/39; A61K 8/02; A61K 8/27; A61K 8/97; A61K 9/0019; A61K 9/107; A61L 2/238; A61L 9/14; A61L 2209/22; A61L 2/23; A61L 2/232; A61L 9/16; A61L 2/16; A61L 2/22; A61L 2202/122; A61L 2202/182; A61L 2/183; A61L 2/186; A61L 2/202; A61L 2/26; A61L 9/014; A61L 9/12; A61L 9/145
See application file for complete search history.

(56) References Cited

U.S. PATENT DOCUMENTS 5,759,939 A    6/1998 Klabunde et al.
5,990,373 A   11/1999 Klabunde
(Continued)

OTHER PUBLICATIONS

International Search Report and Written Opinion dated Sep. 28, 2017, in PCT/US17/40231 filed Jun. 30, 2017.

Primary Examiner — Audrea B Coniglio
(74) Attorney, Agent, or Firm — Hovey Williams LLP

(57) ABSTRACT

Dry mixtures and liquid formulations are provided that comprise metal oxide and/or metal hydroxide nanocrystalline particles. The dry mixtures are advantageously formulated with select surfactants to be readily solubilized and stable in liquid carriers. Additional select components are provided in preferred combinations that are capable of achieving improved biocidal and chemical agent efficacy. Notably, the inventive formulations provided herein allow for easier delivery of the formulations and increased shelf stability.

31 Claims, No Drawings

(51) Int. Cl.
| | |
|---|---|
| *A61K 8/06* | (2006.01) |
| *A01N 25/22* | (2006.01) |
| *C09D 5/03* | (2006.01) |
| *C09D 1/00* | (2006.01) |
| *C09D 5/14* | (2006.01) |
| *C09D 201/00* | (2006.01) |
| *C11D 1/14* | (2006.01) |
| *C11D 1/72* | (2006.01) |
| *C11D 1/831* | (2006.01) |
| *C11D 3/12* | (2006.01) |
| *C11D 1/66* | (2006.01) |
| *C11D 1/00* | (2006.01) |
| *C11D 3/48* | (2006.01) |
| *C11D 17/00* | (2006.01) |
| *C09D 7/45* | (2018.01) |
| *C09D 7/62* | (2018.01) |
| *C09D 7/65* | (2018.01) |
| *C09D 7/63* | (2018.01) |
| *C09D 7/61* | (2018.01) |
| *A01N 25/10* | (2006.01) |
| *A01N 25/30* | (2006.01) |
| *C11D 1/74* | (2006.01) |
| *C11D 3/00* | (2006.01) |
| *C11D 3/20* | (2006.01) |
| *C11D 3/37* | (2006.01) |
| *C11D 3/382* | (2006.01) |
| *C11D 3/43* | (2006.01) |
| *C11D 17/06* | (2006.01) |
| *A61K 8/39* | (2006.01) |
| *A61K 8/46* | (2006.01) |
| *A61K 8/49* | (2006.01) |
| *A61K 8/81* | (2006.01) |
| *A61K 8/88* | (2006.01) |
| *A61K 8/90* | (2006.01) |
| *A61K 8/02* | (2006.01) |
| *A61K 8/04* | (2006.01) |
| *C08K 3/22* | (2006.01) |

(56) References Cited

U.S. PATENT DOCUMENTS

| | | |
|---|---|---|
| 6,057,488 A | 5/2000 | Koper et al. |
| 6,087,294 A | 7/2000 | Klabunde et al. |
| 6,093,236 A | 7/2000 | Klabunde et al. |
| 6,653,519 B2 | 11/2003 | Koper et al. |
| 6,740,141 B2 | 5/2004 | Espin et al. |
| 6,827,766 B2 | 12/2004 | Carnes et al. |
| 6,860,924 B2 | 5/2005 | Rajagopalan et al. |
| 6,887,302 B2 | 5/2005 | Rajagopalan et al. |
| RE39,098 E | 5/2006 | Klabunde et al. |
| 7,279,129 B2 | 10/2007 | Lanz et al. |
| 7,335,808 B2 | 2/2008 | Koper et al. |
| 7,341,977 B2 | 3/2008 | Klabunde et al. |
| 7,473,817 B1* | 1/2009 | Tanaka ............. A61F 13/8405 442/121 |
| 7,566,393 B2 | 7/2009 | Klabunde et al. |
| 7,956,232 B2 | 6/2011 | Koper et al. |
| 8,038,935 B2 | 10/2011 | Koper et al. |
| 8,183,426 B2 | 5/2012 | Cole et al. |
| 2002/0071852 A1 | 6/2002 | Deckers et al. |
| 2005/0045031 A1* | 3/2005 | Rajagopalan .......... B01D 53/02 95/133 |
| 2009/0098016 A1 | 4/2009 | Koper et al. |
| 2009/0118562 A1 | 5/2009 | Cole et al. |
| 2010/0135937 A1* | 6/2010 | O'Brien ................. A61K 8/02 424/59 |
| 2010/0260858 A1* | 10/2010 | Ruddy ................. A61K 9/5078 424/492 |

* cited by examiner

COMPOSITIONS AND METHODS FOR FORMING STABLE, LIQUID METAL OXIDE/HYDROXIDE FORMULATIONS

RELATED APPLICATION

The present application claims the priority benefit of U.S. Provisional Patent Application Ser. No. 62/358,365, filed Jul. 5, 2016, which is incorporated by reference in its entirety herein.

BACKGROUND OF THE INVENTION

Field of the Invention

The invention is generally directed to liquid formulations, or dry formulations that are readily solubilized in a fluid, that comprise metal oxide and/or metal hydroxide nanocrystalline particles. The formulations may be incorporated into fluid streams or applied to surfaces as in coatings or to treat gaseous and liquid phases. The formulations may also be used as a decontaminant for surfaces such as skin, clothing fabric, and other inanimate objects.

Description of the Prior Art

Nanocrystalline metal oxides and hydroxides have been shown to be useful as destructive adsorbents for various malodors and toxic materials, including acid gases, air pollutants, and chemical and biological warfare agents, due to their high surface reactivity (see e.g., U.S. Pat. Nos. 8,183,426, 8,038,935, 7,956,232, 7,566,393, 7,341,977, 7,335,808, 7,279,129, RE39,098, U.S. Pat. Nos. 6,887,302, 6,860,924, 6,827,766, 6,740,141, 6,653,519, 6,093,236, 6,057,488, and 5,990,373, each incorporated by reference herein in its entirety). Liquid formulations of metal oxides and hydroxides have been prepared in aqueous and non-aqueous solvents, along with polymers, surfactants, resins, and/or dispersing agents. However, the metal oxide and hydroxide particles have a tendency to agglomerate in solution. Additionally, it has proven difficult to achieve dry mixtures that are capable of producing stable and usable liquid formulations when added to liquid solution by the end user. Despite the prior work noted above, there is a need for stable, liquid formulations of a nanostructured (nanocrystalline) metal oxides and/or hydroxides, as well as for dry formulations that can be added to liquids at the point of use. Moreover, there is a need for fabric-type products and surface coatings that incorporate nanocrystalline metal oxide/hydroxide particles using stable liquid formulations.

SUMMARY OF THE INVENTION

In one embodiment of the present invention, there is provided a solid powder mixture comprising a quantity of nanocrystalline particles and one or more surfactants selected from the group consisting of ethylene oxide and propylene oxide block copolymers, polysorbates, sodium methacrylates, polyamide-based resin dispersants, sulfosuccinates, and octylphenol ethoxylates. The solid powder mixture may be used to remove a target substance, such as a malodorous target substance, from an article by contacting the mixture with the article and causing at least a portion of the target substance to become adsorbed by the nanocrystalline particles. A liquid suspension may be formulated from the powder mixture. The liquid suspension comprises about 1 part by weight of the solid powder mixture per about 1 part to about 1,000 parts by weight of a liquid carrier. The suspension may be used to treat a surface by applying the liquid suspension to the surface.

In another embodiment, there is provided a liquid composition comprising a mixture of nanocrystalline particles, linseed oil, and a solvent. The liquid composition may be used to sorb a target substance by contacting the liquid composition with the target substance. The liquid composition may also be used to protect a surface by applying the liquid composition to the surface and drying the liquid composition, thereby forming a dry coating comprising nanocrystalline particles on the surface.

In another embodiment, there is provided a liquid composition comprising a mixture of nanocrystalline particles, glycerin, water, and a surfactant. The liquid composition may be used to sorb a target substance by contacting the liquid composition with the target substance. The liquid composition may also be used to clean a surface by applying the liquid composition to the surface and rinsing the liquid composition from the surface.

DETAILED DESCRIPTION OF THE PREFERRED EMBODIMENT

Embodiments of the present invention are directed to dry and liquid formulations that incorporate metal oxides and/or metal hydroxides, more specifically nanocrystalline metal oxides and/or hydroxides, of high surface area and chemical reactivity. The formulations are useful for odor control and sorption, as well as for chemical reactivity with gaseous and liquid agents for destroying, neutralizing, eliminating, and/or protecting against a wide variety of toxic chemicals, noxious odors, and biological hazards.

Preferred nanocrystalline materials for use in connection with the present invention include the metal oxides and metal hydroxides of Mg, Sr, Ba, Ca, Ti, Zr, Fe, V, Mn, Ni, Cu, Al, Si, Zn, Ag, Mo, Sb, and mixtures thereof. Additional preferred nanocrystalline materials include coated nanocrystalline materials such as the metal oxide-coated metal oxides disclosed in U.S. Pat. Nos. 6,093,236, and 5,759,939 (metal oxide coated with another metal oxide), halogenated particles such as the halogen doped metal oxides disclosed in U.S. Pat. Nos. 6,653,519, 6,087,294 and 6,057,488 (nanocrystalline materials having reactive atoms stabilized on the surfaces thereof, the reactive atoms including oxygen ion moieties, ozone, halogens, and group I metals), air stable nanocrystalline materials such as the coated metal oxides described in U.S. Pat. Nos. 6,887,302 and 6,860,924 (nanocrystalline materials coated with a surfactant, wax, oil, silyl, synthetic or natural polymer, or resin), biocidal doped metal oxides, such as silver-doped alumina, and metal oxide or metal hydroxide particles impregnated with a biocide as described in U.S. Pat. No. 6,827,766, pelletized nanocrystalline materials such as those described in U.S. Pat. No. 6,093,236 and U.S. Reissued Pat. No. RE39,098, and composites using agglomerated nanocrystalline particles with a first material coated by second material such as those described in U.S. Pat. Nos. 7,341,977 and 7,566,393, all of which are incorporated by reference herein in their entireties. Therefore, in certain preferred embodiments, the nanocrystalline materials are nanocrystalline (nanostructured) particles selected from the group consisting of MgO, $CeO_2$, CaO, $TiO_2$, $ZrO_2$, FeO, $V_2O_3$, $V_2O_5$, $Mn_2O_3$, $Fe_2O_3$, NiO, CuO, $A_2O_3$, ZnO, $SiO_2$, $Ag_2O$, SrO, BaO, $Mg(OH)_2$, $Ca(OH)_2$, $Al(OH)_3$, $Sr(OH)_2$, $Ba(OH)_2$, $Fe(OH)_3$, $Cu(OH)_2$, $Ni(OH)_2$, $Co(OH)_2$, $Zn(OH)_2$, AgOH, coated metal oxides and hydroxides, doped metal oxides and hydroxides, biocidal metal oxides and hydroxides, and mixtures thereof. The nanocrystalline materials preferably present crystallite sizes of less than about 25 nm, more preferably less 20 than nm, and most preferably less than 10 nm. The nanocrystalline particles preferably exhibit a Brunauer-Emmett-Teller (BET) multipoint surface area of at least about 15 m$^2$/g, more preferably at least about 70 m$^2$/g, and most preferably from about 100-850 m$^2$/g. Powdered metal oxides/hydroxides may be milled to achieve finer particle size. Milling can improve the ability to separate the powders and coat them when done in presence of the surfactants or detergents. The nanocrystalline particles may also be pelletized by compressing or molding powdered metal oxides/hydroxides, for example, in a pellet mill or pellet press. Exemplary nanocrystalline materials are available from Timilon Technology Acquisitions, Inc., Ft. Myers, Florida, under the name NanoActive®.

Preferred surfactants for use in the present invention include tri-block copolymers of polypropylene and polyethylene, such as poloxamers. Poloxamers are nonionic tri-block copolymers having a central hydrophobic chain of polyoxypropylene flanked by two hydrophilic chains of polyoxyethylene. In certain preferred embodiments, the poloxamer has a polyoxyethylene:polyoxypropylene:polyoxyethylene weight ratio of about 4:2:4. It has been surprisingly discovered that poloxamer-type surfactants provide increased stability over other types of surfactants in liquid dispersions containing metal oxide/hydroxide nanocrystalline particles. Particularly preferred poloxamers include those sold under the tradenames of Pluronic® and Synperonic®, for example poloxamer 188 sold under the tradename Pluronic® F-68. In certain embodiments, the one or more surfactants comprise a blend of at least one poloxamer surfactant and at least one other surfactant. For example, in preferred embodiments, the one or more surfactants comprise a blend of a poloxamer (such as p188 poloxamer) and sodium dodecylsulfate (SDS). When the blends include a poloxamer, the weight ratio of poloxamer to the other surfactant may be about 1:20 to about 20:1, preferably about 1:10 to about 10:1, and more preferably about 1:3 to about 3:1.

Other preferred surfactants include polysorbates, sodium methacrylate polyamide-based resin dispersants, sulfosuccinates, and octylphenol ethoxylates. Polysorbates are non-ionic surfactants and are generally composed of polyoxyethylene derivatives of sorbitan monolaurate. Particularly preferred polysorbates include those sold under the tradename Tween®, for example, Tween® 20 and Tween® 81. Sodium methacrylate (sodium polymethacrylate) solutions are water soluble dispersants, generally having relatively low viscosity compared to other solids-based dispersants. Particularly preferred sodium methacrylate dispersants solutions include those sold under the tradename Daxad®, for example, Daxad® 30. Polyamide-based resins show generally low solubility in water and are particularly useful in applications wherein the solution, suspension, or emulsion is being used as a coating. Particularly preferred polyamide resin dispersants include those sold under the tradename Solsperse®, for example, Solsperse® 54000. Sulfosuccinates are generally provided as anionic surfactants, useful in emulsions or in oil-free solutions. Particularly preferred sulfosuccinates include those sold under the tradename Aerosol®, for example, Aerosol® OT (dioctyl sodium sulfosuccinate). Octylphenol ethoxylates are nonionic surfactants useful in emulsions or in oil-free solutions. Particularly preferred octylphenol ethoxylates include those sold under the tradename Triton™, for example, Triton™ X.

Further preferred surfactants include soaps. Soaps are generally a salt of a fatty acid and can typically be obtained by treating vegetable or animal oils and fats with a strongly alkaline solution. A variety of soaps may be used in formulations of the present invention. In preferred embodiments, the soap is castile soap (a soap made from vegetable oils, e.g., olive oil, and sodium hydroxide), coconut oil potassium soap, or a mixture thereof.

One or more additional surfactants may be used in dry or liquid formulations of the present invention. These additional surfactants may be derived from petrochemicals, vegetable oils, and/or animal fats. The additional surfactants may be anionic, cationic, amphoteric, and nonionic. Exemplary anionic surfactants include alkyl sulfates, linear alkyl sulfates, linear alkyl ethoxy sulfates, linear alkyl sulfonates, linear alkylbenzene sulphonic acid, alkyl aryl sulfonates, linear alkene benzene sulphonate, alcohol ether sulfates, laureth sulphates, lauryl ether sulphates, organo-phosphoric acid esters, alkyl aryl sulfates, aryl sulalpha olefin sulphonates, alkyl aryl sulfonates, methyl ester sulphonates, alkylsulfonic acid salts, alcohol sulfates, sodium and ammonium sulphonates, alkyl phosphates, sulfosuccinates, and alkyl phenol ether sulfates. Exemplary cationic surfactants include benzalkonium chloride or bromide, benzethonium chloride or bromide, cetrimonium bromide or chloride, ammonium chlorides, lauryl dimonium chlorides, ammonium hydroxides, alkylpyridinium chlorides and bromides and long chain quaternary ammonium compounds. Exemplary amphoteric surfactants include alkyl betaines, ether amine oxides, cocoamidopropyl dimethyl amine oxides, phospholipids composed of diester and triester phosphatides, and the naturally derived surfactants as lecithins. Exemplary nonionic surfactants include linear or non-phenol alcohols or fatty acids, ethers of fatty alcohols, ethoxylated or ether amines, ethoxylated amines, esters, polysorbates, linear ethylene oxide/propylene oxide and/or butylenes oxide block copolymers, propylamine, glycols, amine oxides, and alcohol ethoxylates and alcohol ethoxysulfates, and alkyl polyglyucosides. In preferred embodiments, the one or more additional surfactants are derived from natural sources or recognized as Generally Recognized As Safe (GRAS). In certain embodiments, the one or more additional surfactants may act as defoaming agents. Particularly preferred defoaming agents included alkyl alcohol ethoxylates, siloxanes, and paraffins.

Liquid carriers for the nanoparticles, surfactants, and/or other components are generally selected from the group consisting of solvents (including aqueous and non-aqueous, as well as organic and inorganic), dispersants, resins, emulsion systems, and combinations thereof. For example, in certain embodiments, the liquid carrier is selected from the group consisting of water, oils, glycerin, organic solvents, halogenated solvents, thickening agents, and mixtures thereof. In certain embodiments, water is the preferred solvent. In certain other embodiments, non-aqueous solvents are preferred and may include organic and halogenated liquids. In certain preferred embodiments, the solvent is an organic solvent, such as mineral spirits (i.e., petroleum-derived organic solvent comprising a mixture of aliphatic and alicyclic $C_7$ to $C_{12}$ hydrocarbons), xylenes, alcohols, toluenes, and the like. For example, in certain preferred embodiments the solvent is methanol. Exemplary halogenated liquid solvents include hydrofluoroether solvents, such as a methyl nonafluorobutyl ether (e.g., HFE-7100 by 3M®). In other preferred embodiments, the solvent is a petroleum-derived organic solvent, such as mineral spirits (paint thinner). Other preferred petroleum-derived solvents include high viscous agents (i.e., thickening agents and gelling agents). Dispersants may be used to create dispersions or suspensions, which are not true solutions. Emulsion systems may be oil-in-water or water-in-oil systems and generally are made up of respective quantities of oil, water, and surfactant. However, in some preferred embodiments the emulsion systems utilize a solvent other than water, such as mineral spirits. The oils may be natural or synthetic. In certain preferred embodiments, the oil is linseed oil. Various resins may also be used as carriers. Resin carriers are particularly useful in applications wherein hard coatings are formed from the compositions. Exemplary resin carriers include siloxane resins and solvent-borne or water-borne Chemical Agent Resistance Coatings (CARC) resins.

Optional additives may also be included in the formulations. For example, pH adjusters may be used to bring the formulations to preferred pH ranges. In certain embodiments, the pH of the liquid formulations is from about 6 to about 10, more preferably from about 7.5 to about 8.5. pH adjusters useful in formulations of the present invention include mineral acids and bases, and organic acids and amines. In preferred embodiments, hydrochloric acid or citric acid is included in the formulation to reduce the pH.

Chemical agents may be used to chelate or sequester metal ions in aqueous solutions so as to soften the water (i.e., reduce water hardness caused by calcium ($Ca^{2+}$) and magnesium ($Mg^{2+}$)). Exemplary chelators include organic acids and salts of ethylene diaminetetraacetic acid, diethylene triamine pentaacetic acid, hydroxyethylene diamine triacetic acid, nitrilotriacetic acid, dihydroxyethyl glycine, methyl glycine diacetic acid, sodium tripolyphosphates, tetrasodium pyrophosphate, hexametaphosphate, tetrapotassium pyrophosphate, bisphosphonates, citrates, tartrates, succinates, gluconates, polycarboxylates, triethanolamine, zeolites, and silicates including sodium disilicate.

Thickeners or friction-reducing agents may be used to achieve the desired viscosity of liquid formulations. Thickener agents are well-reported in the art and included in liquid formulations to increase the viscosity of a liquid without substantially changing its other properties. Exemplary friction-reducing agents include anionic, cationic, or amphoteric polyacrylamides.

Enzymes may be included in the formulations to break down soils and to facilitate soil removal by surfactants (detergents). The enzymes can be selected based upon the specific type of soil being targeted in the formulation. For example, amylases may be included breakdown carbohydrates, proteases included to breakdown proteins, lipases included to breakdown lipids and fats, and/or cellulases included to breakdown celluloses. Antideposition agents may also be included to prevent or deter soils from resettling. Exemplary antideposition agents include sodium carboxy methyl cellulose, polyethylene glycol, polyvinyl alcohol, and polyvinyl pyrrolidone.

Bleaching agents may be included to whiten and/or brighten fabrics and to encourage stain removal. Bleaching agents may be chlorine-based, such as hypochlorite, or non-chlorine based. Exemplary non-chlorine based bleaching agents include perborates and percarbonates, as well as activators to generate hydrogen peroxide or peracetic acid. Optical brighteners may also be included and contain a blue dye or pigment to enhance the light reflected from the fabric, which can make the fabric appear whiter. Exemplary optical brighteners include aminotriazines, coumarins, and stilbenes.

Fabric softeners may be included, particularly in formulations prepared for laundry detergent applications, in order to make fabrics fuller and softer, reducing static cling, wrinkling, and drying time. Exemplary fabric softeners include cationic surfactants, such as long chain quaternary ammonium compounds and long chain amines.

Hydrotropes may be included to achieve preferred pouring characteristics of liquid formulations by preventing gel formation or separation of the formulations. Exemplary hydrotropes include short-chain aromatic sulfonates, such as xylene sulfonate, cumene sulfonate, glycol ether sulphates, and urea.

Preservatives may be included to prevent microorganism growth in formulations, which can help prevent the breakdown of organic constituents. Exemplary preservatives include ethylene diaminetetraacetic acid, diethylene triamine pentaacetic acid, hydroxyethylene diamine triacetic acid, nitrilotriacetic acid, quaternary ammonium chlorides, alcohols, and glutaraldehyde. Fragrances may also be included to add or cover specific smells in the formulation. Particularly preferred fragrances include natural essential oils, which also add antimicrobial properties to the formulation.

Formulations prepared in accordance with the present invention can be prepared as a solid dry powder mixture. For example, in certain preferred embodiments, a solid powder mixture can be prepared comprising (consisting essentially of, consisting of) nanocrystalline metal oxide and/or metal hydroxide particles and one or more surfactants selected from the group consisting of ethylene oxide and propylene oxide block copolymers, polysorbates, sodium methacrylates, polyamide-based resin dispersants, sulfosuccinates, and octylphenol ethoxylates. In preferred dry mixtures, the nanocrystalline particles are present at a level of about 70% to about 99% by weight, preferably about 80% to about 95% by weight, and more preferably about 85% to about 93% by weight, based upon the total weight of the mixture. In such preferred dry mixtures, the one or more surfactants are present at a level of about 1% to about 30% by weight, preferably about 5% to about 20% by weight, and more preferably about 7% to about 15% by weight, based upon the total weight of the mixture. Additionally, in preferred embodiments, the weight ratio of nanocrystalline particles: surfactant is from about 50:1 to about 2:1, preferably from about 40:1 to about 5:1, and more preferably from about 35:1 to about 7:1. The formulations may further comprise other components or additives, such as those described above, as may be desired or required by a particular application. The dry powdered mixtures can be used in their solid form to remove target substance (e.g., a malodorous target substance) from an article by contacting the mixture with the article. Upon contact, at least a portion of the target substance is adsorbed by the nanocrystalline particles.

The solid powder mixtures described above may be added to a liquid carrier to form a liquid suspension. For example, in certain embodiments, the solid powder mixture is added to the liquid carrier (e.g., water, methanol) at a level of 1 part by weight of the solid powder mixture per about 1 part to about 1,000 parts by weight of the liquid carrier, preferably about 2 parts to about 100 parts by weight of the liquid carrier, more preferably about 5 parts to about 50 parts by weight of the liquid carrier, even more preferably about 7 parts to about 20 parts by weight of the liquid carrier, and most preferably about 8 parts to about 12 parts by weight of the liquid carrier.

The liquid suspensions may be prepared by individually adding each component to the liquid carrier or by adding the dry components as a dry powdered mixture. Regardless, the components used in preferred embodiments of the present invention are advantageous in that a mixture of the dry components can be prepared, packaged, transported, stored, and then added to water at the point of use. Prior to the present invention, it had proven difficult to add dry formulations of metal oxide/hydroxide nanocrystalline particles and surfactant to liquids, as liquid suspensions of nanocrystalline particles and surfactant are generally unstable (and unusable) and result in high levels of particle settling. However, formulations prepared in accordance with embodiments of the present invention may be prepared as a dry solid powder that is readily dispersible within a liquid carrier to form a liquid suspension, requiring at most, mild agitation to suspend the particles. The liquid suspensions may also be prepared as gels, creams, or other thickened products. In certain embodiments, the concentration of originally-dry powder mixture in the liquid suspensions is about 1% to about 50%, preferably from about 3% to about 25% by weight, more preferably from about 5% to about 15% by weight, and most preferably from about 7% to about 10% by weight, based upon the total weight of the suspension. In preferred suspensions, the nanocrystalline particles are present at a level of about 0.1% to about 50% by weight, preferably about 0.5% to about 25% by weight, more preferably about 1% to about 12% by weight, and most preferably from about 7% to about 10% by weight, based upon the total weight of the suspension. In such preferred suspensions, the one or more surfactants are present at a level of about 0.01% to about 10% by weight, preferably about 0.05% to about 5% by weight, more preferably about 0.1% to about 2% by weight, and most preferably about 0.5% to about 1% by weight, based upon the total weight of the suspension.

Stable suspensions prepared in accordance with embodiments of the present invention are able to be applied to a variety of surfaces, including hard surfaces and textiles (described in more detail below). For example, suspensions may be applied to surfaces as a liquid, spray, fog, aerosol, paste, gel, wipe, vapor, or foam. Notably, the nanocrystalline particles can remain bonded to surfaces upon application of the suspension, without the use of adhesives, electrostatic attachment, or physical entrapment, although in certain embodiments such methods may be used. In certain embodiments, the suspension is dried after application to the surface. After the suspension is dried, a quantity of the metal oxide/hydroxide nanocrystalline particles remain on the surface (e.g., bonded to the surface) after drying the suspension. In certain other embodiments, the suspension is rinsed from the surface with water after application without drying of the suspension on the surface.

In certain preferred embodiments, the liquid suspension is substantially-free of oil. As used herein, "substantially free" means that the weight percent of the component is less than 0.01%, based upon the total weight of the composition taken as 100% by weight. Surprisingly, it has been discovered that certain oil-free suspensions/solutions demonstrate increased biocidal efficacy (particularly against *Bacillus subtilus* spores) compared to oil/solvent emulsions having identical active ingredients. Certain preferred biocidal suspensions include sulfosuccinates and/or octylphenol ethoxylates as surfactants. Therefore, in certain embodiments, the biocidal suspensions comprise (consist essentially of, consist of) a mixture of nanocrystalline particles and a surfactant selected from the group consisting of sulfosuccinates, octylphenol ethoxylates, and mixtures thereof, in water, and are substantially free of oil. In such embodiments, nanocrystalline particles are present in the suspension at a level of from about 1% to about 50% by weight, preferably from about 5% to about 40% by weight, and more preferably from about 10% to about 30% by weight, based upon the total weight of the suspension. The surfactant is present in the liquid suspension at a level of from about 0.01% to about 10% by weight, preferably from about 0.1% to about 5% by weight, more preferably from about 1% to about 3% by weight, based upon the total weight of the suspension taken as 100% by weight.

The nanocrystalline particles alternatively may be provided in stable liquid formulations that do not utilize the surfactants discussed above. For example, in a preferred embodiment, a stable liquid composition is provided comprising (consisting essentially of, consisting of) a mixture of nanocrystalline particles, linseed oil, and a solvent. In certain preferred embodiments, the solvent is an organic solvent (such as mineral spirits) or a halogenated solvent. In such embodiments, nanocrystalline particles are present in the liquid composition at a level of from about 30% to about 60% by weight, preferably from about 50% to about 60% by weight, and more preferably about 52% to about 58% by weight, based upon the total weight of the composition. Linseed oil is present in the liquid composition at a level of from about 5% to about 30% by weight, preferably from about 5% to about 15% by weight, and more preferably about 9% to about 11% by weight, based upon the total weight of the composition. Solvent is present in the liquid composition at a level of from about 20% to about 50% by weight, preferably from about 25% to about 45% by weight, and more preferably about 30% to about 40% by weight, based upon the total weight of the composition. In particularly preferred embodiments, the solvent is mineral spirits (i.e., paint thinner). The particular combination of nanocrystalline particles, linseed oil, and solvent results in a liquid composition that is advantageously easy to spray, adheres to a wide variety of materials, and can be easily removed once dry.

Liquid compositions comprising (consisting essentially of, consisting of) a mixture of nanocrystalline particles, linseed oil, and solvent, may be used to sorb a target substance (e.g., harmful chemical agents and/or malodorous substances) by applying the composition to a space and/or a surface containing the target substance. The target substance is sorbed by contacting the liquid composition with the target substance under conditions for sorbing at least a portion of the target substance. Alternatively, the liquid compositions may be used to prevent or deter contamination of a target substance. For example, the liquid composition may be applied to a hard surface or textile surface and dried, thereby creating a dry coating comprising the nanocrystalline particles the surface.

In another preferred embodiment, a stable liquid composition is provided comprising (consisting essentially of, consisting of) a mixture of nanocrystalline particles, glycerin (e.g., vegetable glycerin), water, and a surfactant. In certain embodiments, the nanocrystalline particles are present in said composition at a level of from about 1% to about 10% by weight, preferably about 3% to about 8% by weight, and more preferably about 4% to about 6% by weight, based upon the total weight of the composition. Glycerin is present in said composition at a level of from about 1% to about 30% by weight, preferably about 5% to about 20% by weight, and more preferably about 8% to about 12% by weight, based upon the total weight of the composition. Water is present in said composition at a level of from about 1% to about 30% by weight, preferably about 5% to about 20% by weight, and more preferably about 8% to about 12% by weight, based upon the total weight of the composition. The surfactant is present in said composition at a level of from about 50% to about 90% by weight, preferably about 60% to about 80% by weight, and more preferably about 70% to about 75% by weight, based upon the total weight of the composition. In particularly preferred embodiments, the surfactant is a soap.

Liquid compositions comprising (consisting essentially of, consisting of) a mixture of nanocrystalline particles, glycerin, water, and a surfactant, may be used to clean a surface or sorb a target substance by applying the compositions to a surface having the target substance and rinsing the composition from the surface. In particularly preferred embodiments, the surface is skin (e.g., human skin). In such embodiments, the liquid compositions are useful as an antibacterial disinfectant such as hand soap. In other preferred embodiments, the surface is a surface of an inanimate object, such as "hard" surfaces used in food preparation, hospitals, and the like. In such embodiments, the liquid compositions may be used to decontaminate the object surface and make the object safe for human use and handling.

Formulations prepared in accordance with embodiments of the present invention are useful for a variety of applications. Advantageously, in certain embodiments mixtures of the dry components as described herein can be packaged and sold to an end user, and the dry components can be added to liquid at the point of use before application. One exemplary application is a laundry detergent product, which can be prepared as a liquid or as a dry mixture. Detergent applications may also include various laundry additives (so called builders) to adjust pH, chelate, and bind metals to reduce hardness.

Formulations may also be used as a biocide or decontaminant on soft or hard surfaces. The inventive formulations may be used as effective biocides against vegetative bacterial organisms, such as *Escherichia coli* and *Staphylococcus aureus*. Exemplary soft surfaces include a textile material selected from the group consisting of carpets, upholstery, fabrics (including clothing fabrics), paper products, leather, and combinations thereof. In certain preferred embodiments, the formulations are applied to a textile surface, for example, a woven or non-woven textile surface. In such embodiments, useful articles may be prepared. For example, chemical decontamination wipes may be prepared by applying a liquid formulation of the present invention to the wipe and drying the formulation, thereby leaving solid nanocrystalline particles bonded to the wipe. The wipe can be used as a disinfecting or chemical decontamination wipe that will leave little or no solid or liquid residue, and that can convert chemical warfare agents (CWAs) into less toxic or even nontoxic compounds. Zinc and copper oxides are particularly preferred nanocrystalline materials for applications where the wipe is used as anti-microbial wipe against *Staphylococcus aureus, Klebsiella pneumoniae,* and *Escherichia coli*. Particularly suitable fabrics for use as wipes include Polartec® Power Dry, a polyester made by Malden Mills, Lawrence, Mass.; Dryline®, a 71% nylon, 12% polyester, 17% Lycra material made by Milliken & Co.; Spartanburg, S.C., Coolmax®, a 52% Tactel nylon, 39% polyester, 9% Lycra fabric made by Invista Co., Wichita, Kans.; Coolmax® Doubleplay, a 100% polyester material also made by Invista; Wickaway® terry Lycra, a polyester from Seattle Fabrics, Seattle, Wash.; Under Armour®, a nylon/polyester/elastin fabric made by Under Armour Inc., Baltimore, Md.; Dryskin®, an 80% nylon, 15% polyester, 5% Lycra made by Schoeller Textil AG, Sevelen, Switzerland; and the fabric from the inner layer used in Huggies® disposable diapers, Kimberly-Clark Global Sales, Inc., Neenah, Wis. In the most preferred embodiment, the fabric is Dryline®.

In other preferred embodiments, the formulations may be applied to a textile for use as a reactive liner insert for chemical protective clothing (CPC). The liners maybe be used, for example, as a Class II Protective Garment for 2-CEES, HCN, $NH_3$, and DMMP.

Exemplary hard surfaces include non-textile materials such as plastic, metal, wood, drywall paint, foam, and combinations thereof. The formulations may be applied to any of the above soft or hard surfaces as a liquid or vapor, for example as a spray, fog, aerosol, paste, gel, wipe, or foam. In certain embodiments, the soft or hard surfaces can be in an enclosed space (e.g., a room with little or no air circulation). The formulations may also be incorporated into a resinous substance and applied to a hard surface, thereby forming a biocidal coating on the surface. Such coatings are particularly effective against vegetative bacterial organisms, such as *Escherichia coli* and *Staphylococcus aureus*.

In preferred embodiments, the nanocrystalline particles bond to the surface (e.g., hard surface or textile surface) without the use of adhesives, electrostatic attachment, or physical entrapment. However, in other embodiments, traditional adhesives and methods may be used to bond the particles onto the surfaces. Traditional laminations can be loosely defined as the bonding of materials utilizing conventional equipment and commercially available adhesive systems, which are readily used and have well known chemistries. For the most part, the performance of these adhesives and equipment are well understood and has an extensive history within the textile industry. Examples of traditional adhesives are UV curable, pressure sensitive, hot melt, instant and water based.

In preferred embodiments, the formulations are particularly suitable for odor control. For example, where a surface is contaminated with a malodorous substance, applying the inventive liquid suspensions to the surface can cause at least a portion of the malodorous substance to become adsorbed by the nanocrystalline particles in the suspension. Exemplary odors and malodorous substances that can be adsorbed include animal odors, animal waste odors, asphalt fumes, charred materials, cleaning chemicals, decaying bodies, decaying vegetation, detergents, disinfectants, diapers, exhaust, fuel (i.e., gasoline/diesel), volatile organic compound fumes (e.g., paint, varnish, and solvent odors), organic solvents, odors caused by moisture or flooding (i.e., mold and mildew), human body odors (i.e., sweat, bacterial infections, urine and fecal odors) hunting odors (i.e., deer urine), pesticides, kitchen odors (i.e., refrigerator odors, burnt food, cooking odors, fish, poultry, garlic, onion, rancid oils), medicinal odors, sewer gases, smoke (e.g., tobacco smoke odors), garbage, other odors caused by bacteria, mildew, and fungi, and combinations thereof. Volatile organic compounds that may be adsorbed by the nanocrystalline particles include acrolein, acetone, ethanolamine, diesel fuel, formaldehyde, hydrofluoric acid, methanol, methylene chloride, nitric acid, nitrobenzene, phosphoric acid, polyvinyl alcohol, sulfuric acid, thiourea, toluene, triethanolamine, methyl acrylate, acetic acid, methylpyrazines, acrylonitrile, nonvolatile nitrosamines, crotonaldehyde, N-nitrosamines, carboxylic acids, phenols, DDT/delirin, pyrrolidine, dimethylnitrosamine, stearic acid, ethylamine, trimethylamine, vinyl chloride, furfural, and combinations thereof.

Notable advantages of the present invention include easier delivery of the metal oxides/hydroxide formulations and higher shelf stability. The liquid suspensions demonstrate increased stability over prior art particle/surfactant/carrier solutions. For example, liquid suspensions in accordance with certain embodiments of the present invention having one gram of the nanocrystalline particles dispersed within 10 mL of water demonstrate less than 50% particulate settling for at least 3 minutes, preferably at least 5 minutes, more preferably at least 10 minutes, and most preferably at least 18 minutes after agitation. Additionally, liquid suspensions prepared in accordance with certain embodiments of the present invention remain physically stable for at least about 4 days under quiescent storage conditions at 25° C., and settled suspensions can be easily re-suspended by simple agitation (e.g., shaking). The formulations of the present invention also achieve desirable odor control, even in formulations containing a surfactant. For example, where solid powdered mixtures or dried suspension residues prepared in accordance with embodiments of the present invention are contacted with diethylamine in an enclosed spaced, the contacting results in at least about a 75% reduction, preferably at least about an 80% reduction, and most preferably at least about an 87% reduction in the concentration of diethylamine in the enclosed space. Moreover, the formulations of the present invention achieve better penetration of the metal oxides/hydroxides into fabrics, textiles, and other porous and non-porous materials. Additionally, the formulations provide improved, more uniform coatings as applied to various surfaces preventing powdery fumes or powdery waste. Other advantages will be apparent from the examples provided below and in the claims.

EXAMPLES

The following examples set forth formulations and efficacy testing based upon embodiments of the present invention. It is to be understood, however, that these examples are provided by way of illustration and nothing therein should be taken as a limitation upon the overall scope of the invention.

Example I

Determination of Surfactants' Ability to Stabilize Powder. Tests were performed using two nanocrystalline particle powder blends (Formulations 1 and 2) and several surfactants or surfactant blends. Formulation 1 was a 50/25/25 blend of MgO/ZnO/TiO2 of nanocrystalline particles, and Formulation 2 was an 80/20 blend of MgO/ZnO nanocrystalline particles. The surfactants were sodium dodecylsulfate (SDS), an anionic surfactant, poloxamer 188 (Pluronic® F-68), a nonionic surfactant, blends of poloxamer 188 and SDS, and a fatty alcohol sulphate (Ufarol®), an anionic surfactant.

One gram of powder and a measured amount of surfactant were mixed dry in a 4-dram vial followed by addition of 10 mL of water. The vial was mixed thoroughly and then allowed to sit. A timer was used to measure the amount of time for the powder level to settle to one half of the initial volume, allowing for comparisons across samples. Results are shown in Table 1 below.

TABLE 1

Surfactant/Powder Stability.

| Powder | Surfactant | Surfactant Weight (g) | Settling time (min) | Comments |
|---|---|---|---|---|
| Formulation 1 | none | n/a | 4.75 | |
| | P188 | 0.2 | <5.5 | |
| | | 0.1 | 12 | Some foaming |
| | SDS | 0.05 | 3 | |
| | | 0.1 | — | Excessive foaming, two layers formed w/ upper foam layer not settling |
| | | 0.05 | — | |
| | P188/SDS | 0.01/0.09 | 3.33 | |
| | | 0.025/0.075 | 2.5 | |
| | | 0.05 each | 4.5 | |
| | | 0.075/0.025 | 5.0 | |
| | | 0.09/0.01 | 5.0 | |
| | Ufarol® | 0.1 | 2.5 | Significant foaming |
| Formulation 2 | none | n/a | 3.5 | |
| | P188 | 0.2 | 6.25 | Excessive foaming |
| | | 0.1 | ~18 | Did not settle to 50%; Reached ~55% in ~18 minutes |
| | SDS | 0.1 | — | Excessive foaming, two layers formed w/ upper foam layer not settling |
| | P188/SDS | 0.01/0.09 | ~8 | Did not settle to 50% |
| | | 0.025/0.075 | 4 | |
| | | 0.05 each | 2 | |
| | | 0.075/0.025 | 2.25 | |
| | | 0.09/0.01 | 2.25 | |
| | Ufarol® | 0.1 | 3.5 | Significant foaming; Did not settle to 50%; Reached ~60% in 3.5 minutes |

Of the combinations tested, poloxamer 188 at a final concentration of 0.9% yielded the best stability of powder in solution (powder concentration of 9%). Formulation 2 showed slightly better stability than Formulation 1, especially with the P188 surfactant.

Ability to Spray. Formulation 1 and Formulation 2 powders were individually mixed in a bottle with poloxamer 188 surfactant (35 g powder, 3.5 g surfactant) then added to 0.35 L of water in a Professional grade spray bottle. This yielded a final composition of 9% powder and 0.9% surfactant. The mixture was shaken well and then sprayed onto a surface. The bottle was allowed to sit for approximately 4 hours and then shaken well. The mixture was then sprayed again if possible. This was also repeated after sitting overnight.

The Formulation 1 suspension sprayed evenly, but there were occasions where the spray bottle had difficulty spraying the material. After the 4-hour wait period, the suspension had settled noticeably, but upon shaking the material mixed easily. However, the spray bottle would not discharge any material when attempting to spray. After cleaning the spray head with water, the spray bottle worked again, although there were times when squeezing the trigger was difficult as if the spray head was clogging again. This was also the case after the overnight wait period. In all cases, once the discharged suspension had dried, there appeared to be an even coating of powder across the surface.

The Formulation 2 suspension also sprayed evenly, and there were no difficulties spraying the material. After the 4-hour wait time, the material had settled but easily mixed back into solution when shaken. After a few pumps to clear the nozzle, the spray bottle was able to discharge the suspension without requiring cleaning. This was also the case after the overnight period. As with the Formulation 1 suspension, all spray periods yielded an even coating of powder once allowed to dry.

The Formulation 2 suspension was then transferred to a basic spray bottle which sprayed the suspension with no difficulties. The bottle was allowed to sit for 4 days and then sprayed again with no clogging.

Example II

Determination of Surfactants' Ability to Stabilize Powder. Tests were performed using Formulation 1 and Formulation 2 powders and several surfactants. All surfactants were dry except Tween® 20 (polysorbate 20, polyoxyethylene derivative of sorbitan monolaurate) and Daxad® 30 (sodium polymethacrylate solution having 25% solids content by weight). The Pluronic® surfactants include various poloxamers having different molecular weight.

One gram of powder and 0.1 g of surfactant were added to a 4-dram vial followed by addition of 10 mL of water. The vial was mixed thoroughly and then allowed to sit. A timer was used to measure the amount of time for the powder level to settle to one half of the initial volume, allowing for comparisons across samples. Results are shown in Table 2 below.

TABLE 2

Surfactant/Powder Stability.

| Powder | Surfactant | Settling time (min) | Comments |
|---|---|---|---|
| Formulation 1 | none | 4.75 | |
| | Poloxamer 188 | 12 | Some foaming |
| | SDS | | Excessive foaming, two layers formed w/ upper foam layer not settling |
| | Ufarol ® | 2.5 | Significant foaming |
| | Pluronic ® F-38 | 4 | |
| | Pluronic ® F-87 | 3.33 | |
| | Pluronic ® F-108 | 3 | |
| | Tween ® 20 | 3 | |
| | Daxad ® 30 | <8 | |
| Formulation 2 | none | 3.5 | |
| | P188 | ~18 | Did not settle to 50%; reached ~55% |
| | SDS | — | Excessive foaming, two layers formed w/ upper foam layer not settling |
| | Ufarol ® | 3.5 | Significant foaming; Did not settle to 50%; Reached ~60% in 3.5 minutes |
| | Pluronic ® F-38 | 8.75 | Did not settle to 50% |
| | Pluronic ® F-87 | 7 | |
| | Pluronic ® F-108 | 5 | |
| | Tween ® 20 | 13 | |
| | Daxad ® 30 | 7 | |

Of the combinations tested, poloxamer 188 at a final concentration of 0.9% yielded the best stability of powder in solution (powder concentration of 9%). Like in the previous examples, the Formulation 2 suspension showed slightly better stability than Formulation 1. This study points to the importance of structure and chemistry of the surfactants in stabilizing the nanostructured metal oxides. With the Pluronic® nonionic polypropylene and polyethylene block copolymer surfactants studied (F-38, F-68, F-87, and F-108) differences were seen in the stabilization of the metal oxide particles. For these surfactants, the molecular weights increase from 4700 for F-38, to 8400 for F-68, to 7700 for F-87, to 14,600 for F-108. For these surfactants, the hydrophile/lipophile balance (HLB) go from 31, to 29, to 24, to 27, respectively. Surprisingly, the Pluronic® F-68 (poloxamer 188) was shown to be a preferred Pluronic® for stability.

Example III

Previous testing of dry surfactants indicated that poloxamer 188 (P188) had the best ability to stabilize Formulation 1 powder in suspension. The focus of the previous testing was on the stability of the powder in suspension. Additional testing was performed in triplicate to determine the efficacy of the suspensions with and without surfactant (P188). A portion of each suspension (with and without P188) was dried to a powder.

Suspensions of Formulation 1 were prepared using 70 g of Formulation 1 powder suspended in 700 mL of water. For the suspension with surfactant, 0.7 g of poloxamer 188 was then added. Suspensions were then mixed well. A portion, approximately 300 g of each suspension, was also dried to a powder in an oven at 105° C. and tested for efficacy.

For the liquid suspension, efficacy was determined by using "Surface Test" against skunk thiol. In the Surface Test, a section or carpet was treated with skunk odor followed by treatment with the Formulation 1 suspension. The square was then rinsed and allowed to air dry, at which point the square was smelled to determine if there was a noticeable decrease in the skunk odor. If a noticeable decrease in odor was achieved, the test outcome was recorded as a "Pass."

For the dried powder, efficacy was tested using "Odor Efficacy" against diethylamine. In the Odor Efficacy test, a measured amount of sorbent powder was sealed in a vial with a measured amount of diethylamine (typically at a 25:1 sorbent:agent ratio). The gas headspace in the vial was then sampled and analyzed by GC-FID. The amount of agent present was then compared to a vial with no sorbent to determine the % Agent Removed.

Additionally, surface area of the dried powders was measured to determine if the presence of surfactant decreased the surface area of the Formulation 1 powder. Results are shown in the Table 3 below.

TABLE 3

Surfactant Effect on Efficacy.

| | | Powder Tests | | Suspension |
|---|---|---|---|---|
| Sample | Replicate | Odor Efficacy (% Removed) | Surface Area ($m^2/g$) | Test Surface Test |
| Form. 1 w/o P188 | 1 | 91 | 130 | Pass |
| | 2 | 100 | 134 | Pass |
| | 3 | 100 | 128 | Pass |
| | Average | 97 | 131 | — |
| | St. Dev. | 5.2 | 3.1 | — |
| Form. 1 w/ P188 | 1 | 75 | 124 | Pass |
| | 2 | 100 | 131 | Pass |
| | 3 | 87 | 121 | Pass |
| | Average | 87 | 125 | — |
| | St. Dev | 12.5 | 5.1 | — |

As can be seen by the results, the presence of P188 surfactant had only a small effect on Odor Efficacy and surface area of the dried powder. For unprocessed Formulation 1 powder (same lot used to prepare suspensions), the Odor Efficacy was 99% removed and the surface area was 281 $m^2/g$ (data not shown in Table 3). This data suggests that surface area is not the key parameter in efficacy since unprocessed Formulation 1 powder has a very high surface area but near comparable efficacy. A two-tailed t-test of the Odor Efficacy data yields a P value of 0.188, indicating that there is no statistical difference between efficacy of Formulation 1 with and without surfactant. A likely explanation is that the surfactant molecules do not inhibit the diethylamine from penetrating the pores which allows those pores to remain active when exposed to a chemical agent. The performance specification of Formulation 1 powder Odor Efficacy is greater than 80% removed. Even with the non-statistical decrease in efficacy of the processed sample with surfactant, the material still exceeds the minimum performance specification.

Example IV

In this example, the stability of milled nanocrystalline particulates were tested in an organic solvent (methanol) liquid carrier, using a variety of different surfactants.

A 65/35 blend of MgO/$TiO_2$ of powdered metal oxides/hydroxides were milled to make them finer in particle size with either the surfactant being present during milling (grinding) or the surfactant being added after milling. Surfactants tested included DAXAD® 30 (sodium polymethacrylate solution having 25% solids content by weight), Tween® 81 (polyoxyethylene derivative of sorbitan monolaurate), and Solsperse® 54000 (polyamide resin-based dispersant). Suspensions were prepared in methanol solvent and the stability of the suspensions were tested. Results are shown in Table 4 below.

Notably from the data above, higher surfactant concentrations do not necessarily improve stability of the liquid suspensions.

Example V

In this example, an alternative liquid carrier and surfactant-free formulations were tested for efficacy as a decontaminant or preventative coating.

Several sprayable liquid binder fluids were evaluated for adhesion of the powdered decontaminant to walls, ceilings, and other surfaces, while retaining the reactivity of the sorbents. A preferred mixture included a mixture of linseed oil, paint thinner, and $TiO_2$ nanocrystalline particles. This combination was easy to spray, adhered to a wide variety of materials, and was easily removed once dry.

A mixture of 55 wt % $TiO_2$ nanocrystalline particles, 10 wt % boiled linseed oil, and 35 wt % mineral spirits (paint thinner) was formulated as an alternative to the water-based formulations containing commercially-available water-based acrylic binders. Paint thinner and linseed oil were mixed thoroughly before the $TiO_2$ particles were added to the formulation. The new, linseed oil-based formulation was tested for decontamination of diisopropyl methylphosphonate (DIMP, a water insoluble nerve agent simulant) and 2-chloroethyl ethyl sulfide (2-CEES, a sulfur mustard simulant). The simulants were applied to glass coupons at a rate of 10 g/$m^2$, and the decontaminant at a rate of 10 grams of

TABLE 4

Suspension Stability Data for 65/35 blend of MgO/$TiO_2$ milled particles in methanol.

| Sample | Surfactant Concentration | Addition Time | Grinding Time | % Solids | Stability | Particle Size-Wet (μm) |
|---|---|---|---|---|---|---|
| 1 | 0 | NA | NA | 21 | Stable | 1.7 |
|   |   |   |   | 20 |   | 1.4 |
|   |   |   |   | 20 |   | 1.6 |
| 2 | 2% DAXAD ® 30 | To suspension before grinding | 15 min | 15 | Stable | 1.9 |
| 3 | 2% DAXAD ® 30 | To suspension before grinding | 1 hour | 15 | Stable | 3.8 |
| 4 | 5% DAXAD ® 30 | To suspension before grinding | 15 min | 16 | Unstable | 1.3 |
| 5 | 5% DAXAD ® 30 | To suspension before grinding | 30 min | 15 | Stable | 1.2 |
| 6 | 5% DAXAD ® 30 | To suspension before grinding | 1 hour | 14 | Stable | 2.4 |
|   |   |   |   |   |   | 4.5 |
| 7 | 2% DAXAD ® 30 | To suspension after grinding | NA | 17 | Stable | 1.4 |
| 8 | 5% DAXAD ® 30 | To suspension after grinding | NA | 17 | Stable | 0.90 |
| 9 | 10% DAXAD ® 30 | To suspension after grinding | NA | 14 | Unstable | 0.26 |
| 10 | 2% Tween ® 81 | To suspension before grinding | 15 min | 17 | Stable | 1.8 |
| 11 | 2% Lubrizol ® 2% Solsperse ® 54000 | To suspension before grinding | 1 hour | 15 | Stable | 2.5 |
| 12 | 2% Solsperse ® 54000 | To suspension after grinding | NA | 19 | Stable | 1.0 |
| 13 | 5% Solsperse ® 54000 | To suspension after grinding | NA | 21 | Stable | 1.6 |
| 14 | 2% Tween ® 81 | To suspension after grinding | NA | 17 | Stable | 0.99 |
| 15 | 5% Tween ® 81 | To suspension after grinding | NA | 20 | Stable | 0.83 |
| 16 | 0 | NA | 1 hour | — | — | 0.59 |
| 17 | 0 | NA | 1 hour | 17 | Stable | 0.89 |

NA = Not Applicable.

sorbent per gram of simulant (180 g of formulation per square meter). After 15 or 30 minutes (before the coating had dried), coupons were extracted with hexane, and the extracts were analyzed for remaining agent by GC. The linseed oil-based formulations possessed excellent decontamination activity against DIMP, showing 99.8% decontamination in 15 minutes. After 30 minutes, extraction showed that the level of DIMP present had dropped below the limit of detection. Extraction after 30 minutes showed decontamination of 83.6% of the 2-CEES.

Coating tests using glass, tile, aluminum, and polycarbonate surfaces demonstrated that the formulation leaves an even coat when applied vertically, and adheres well to the surfaces. The resultant coating was dry to the touch after 60-90 minutes, and was completely dry when left overnight. Clean-up was easy, as the resultant coating can be removed by light brushing or vigorous tapping; the coating flakes off in fairly large pieces rather than as a dust. Nearly 100% of the sprayed formulation adhered to the surface, and little if any is wasted as overspray. It can be sprayed from a variety of commercially available sprayers, adheres to horizontal, vertical, and upside-down surfaces, dries in about an hour, and dries thoroughly overnight. The dried coating can be removed by brushing, water spraying, or air blowing, leaving a clean surface.

Example VI

In this example, water-based suspensions were tested against water/oil emulsions for biocidal activity.

Study on *Bacillus subtilus* spores. Various types of emulsions were tested for biological activity, the most effective formulations contained AP—CaO, AP—Ca(OH)$_2$, and AP—MgO nanoparticles. The samples were prepared by adding approximately 0.04 g of surfactant to about 5 mL aqueous solution. The aqueous solutions comprised approximately 10% by weight of oil and 5% by weight of the nanoparticles. Two types of surfactants were used in the samples, dioctyl sodium sulfosuccinate (Aerosol OT, AOT) and polyethylene glycol tert-octylphenyl ether (Triton-X) in the emulsion. The formulations were also tested in a water-surfactant only solution (no oil), and the efficacy of the solutions was compared to the emulsions. The results are shown in Table 5 below.

TABLE 5

Effects of Various Nanoparticle Containing Emulsions or Solutions on *Bacillus subtilus* spores after 24 hours

| Components of emulsions/solutions | Percent kill of B. subtilus spores after 24 hours of contact | Log Reduction |
|---|---|---|
| AP-MgO/AOT/water (no oil) | 99.7 | 1.52 |
| AP-Mg(OH)$_2$/AOT/water/oil | 0 | 0 |
| AP-Mg(OH)$_2$/Triton-X/water/oil | 0 | 0 |
| AP-Mg(OH)$_2$/AOT/water(no oil) | 86.9 | 0.882 |
| AP-Mg(OH)$_2$/Triton-X/water(no oil) | 64.3 | 0.447 |
| AP-Ca(OH)$_2$/AOT/water/oil | 99.9 | 3.00 |
| AP-Ca(OH)$_2$/Triton-X/water/oil | 97.3 | 1.56 |
| AP-Ca(OH)$_2$/AOT/water (no oil) | 99.8 | 2.69 |
| AP Biocide Efficacy Coupons were composed of a steel substrate overlaid with a primer coat and topped with various resin types. The primer coat which was generally used contains zinc. Many different resins (siloxane, solvent-borne or water-borne Chemical Agent Resistance Coatings (CARC), and others) were used. The biocidal activity of the coupon components and resins was determined by ASTM 2180 as previously described, using E. coli and S. aureus as the challenge organisms. Tables 8 and 9 display the results.

TABLE 8

ASTM E 2180-01 Testing Results for Escherichia coli.

| Entry | ID | Description | Log Kill | % Kill |
|---|---|---|---|---|
| 9 | SC | Steel Control (no primer) | BDL | BDL |
| 10 | S9 | Sanded Steel (9 micron paper) | BDL | BDL |
| 11 | ZPC | Zinc Phosphate Control | BDL | BDL |
| 12 | ZP9 | Sanded Zinc Phosphate (9 micron paper) | BDL | BDL |
| 13 | EC | E-coat Control | 1.4 | 92.5 |
| 14 | E9 | Sanded E-coat (9 micron paper) | 1.1 | 91.4 |

*BDL: Below Detection Limit. No bacteria were recovered in the counting plates from these coupons

TABLE 9

ASTM E 2180-01 Testing Results for Staphylococcus aureus.

| Entry | ID | Description | Log Kill | % Kill |
|---|---|---|---|---|
| 15 | SC | Steel Control | BDL | BDL |
| 16 | S9 | Sanded Steel (9 micron paper) | BDL | BDL |
| 17 | ZPC | Zinc Phosphate Control | BDL | BDL |
| 18 | ZP9 | Sanded Zinc Phosphate (9 micron paper) | BDL | BDL |
| 19 | EC | E-coat Control | −0.37 | — |
| 20 | E9 | Sanded E-coat (9 micron paper) | 0.85 | 41.9 |

*BDL: Below Detection Limit. No bacteria were recovered in the counting plates from these coupons As shown Tables 8 and 9, the S. aureus was more resistant to any antibacterial activity resulting from the coupon components than the E. coli. The antibacterial activity of the zinc phosphate was expected; however, the activity of the steel control was unexpected. Once the biocidal activities of the coupon components were known, test finished coupons were tested. Some of the control resins (unmodified resins without nanocrystalline material) were weakly biocidal, with <2 log kill against the 2 challenge organisms.

Initially, the ASTM test method was utilized as written. However, during the course of testing an issue arose regarding the test results. During an early round of coupon testing, it was noticed that several of the coupons appeared to have strong biocidal activity against Staphylococcus aureus, but not Escherichia coli. This result was contrary to the reported disinfection resistance of the 2 organisms, as gram (−) organisms are commonly more susceptible to disinfectants, while gram (+) organisms are more resistant. Further investigation showed the resins used to produce these coupons were strongly hydrophobic. Staphylococcus aureus is known to bind strongly to hydrophobic surfaces, a capability which enables them to resist removal during washing. If the S. aureus were binding tightly to the surface of the coupons, no cells would be recovered during the ASTM vortexing step. Consequently, no colonies would grow on the agar plate, and the coupon would appear to be highly biocidal. In order to ensure that biocidal activity seen during the ASTM testing was genuine, test method was modified slightly to add a confirmation step. Note that the confirmation step was only performed if the coupon demonstrated good biocidal activity against S. aureus.

Following this initial success, a number of biocidal coupons with different loading levels of biocidal nanocrystalline materials were produced. Some of the coupons were also subjected to post-production processing, including plasma cleaning, to expose more of the nanocrystalline materials on the coupon surfaces. The incubation period for this assay was 24±2 h.

Table 10 lists the finished coupons and shows biocidal activity.

TABLE 10

Finished Coupons with Biocidal Activity

| Entry | Description | Log Kill E. coli | Log Kill S. aureus |
|---|---|---|---|
| 21 | 14.5% Silver Modified RNP 989 in Modified Siloxane in CARC Resin | >7.2* | 3.7 |
| 22 | 13% Silver Modified RNP 989 in Modified Siloxane and 15% RNP 990 in CARC Resin | 6.5 | >5.2* |
| 23 | 14.5% Silver Modified RNP 989 in Modified Siloxane in CARC Resin with Plasma Cleaning | >6.0* | >5.2* |
| 24 | 13% Silver Modified RNP 989 in Modified Siloxane and 15% RNP 990 in CARC Resin with Plasma Cleaning | >6.0* | >5.2* |
| 25 | 20% Silver Modified RNP 989 (D141-102708) in Waterborne CARC Resin with Modified Siloxane with Plasma Cleaning | >6.0* | >5.2* |
| 26 | 20% Silver Modified RNP 989 in Waterborne CARC Resin with Modified Siloxane | 5.5 | 3.4 |
| 27 | SB CARC + grind double concentration (siloxane + Ag—Al2O3) | ≥8.0* | ≥7.7* |
| 28 | SB CARC + MgO + Ag—Al2O3 | 7.7 | ≥7.7* |
| 29 | SB AF Black + 32% MgO/siloxane grind | 6.5 | 5.6 |

*BDL: Below Detection Limit. No bacteria were recovered in the counting plates from these coupons Looking at the results in Table 10, there are some noticeable trends. Firstly, plasma cleaning of biocidal coupons increased biocidal activity. Secondly, silver modification of the RNPs was required, with the exception of Entry 29.

CONCLUSIONS

The performance of the biocidal coupons against vegetative bacteria is extremely good. The >3 log reduction is sufficient to classify the coatings as sporicidal under the E.U. standard. This example established the feasibility of incorporating the nanocrystalline materials into a variety of coatings. Biological activity was clearly enhanced by the inclusion of the nanocrystalline materials. Time-kill studies show that the biological activity begins to impact the number of challenge organisms measurably within 1 h and leads to a >5 log reduction within 3 h. This level of biological activity could be extremely useful in a medical or public health setting.

We claim:

1. A solid dry powder mixture comprising a quantity of dry powder nanocrystalline metal oxide and/or metal hydroxide particles and one or more dry powder surfactants selected from the group consisting of ethylene oxide and propylene oxide block copolymers, polysorbates, sodium methacrylates, polyamide-based resin dispersants, sulfosuccinates, and octylphenol ethoxylates, wherein the nanocrystalline metal oxide and/or metal hydroxide particles are agglomerated nanocrystalline materials, and wherein the powder mixture is readily dispersible in a liquid carrier and remains physically stable for at least 4 days under quiescent storage conditions at 25° C.

2. The mixture of claim 1, wherein said nanocrystalline particles are selected from the group consisting of MgO, $CeO_2$, CaO, $TiO_2$, $ZrO_2$, FeO, $V_2O_3$, $V_2O_5$, $Mn_2O_3$, $Fe_2O_3$, NiO, CuO, $Al_2O_3$, ZnO, $SiO_2$, $Ag_2O$, SrO, BaO, $Mg(OH)_2$, $Ca(OH)_2$, $Al(OH)_3$, $Sr(OH)_2$, $Ba(OH)_2$, $Fe(OH)_3$, $Cu(OH)_2$, $Ni(OH)_2$, $Co(OH)_2$, $Zn(OH)_2$, AgOH, coated metal oxides and hydroxides, doped metal oxides and hydroxides, biocidal metal oxides and hydroxides, and mixtures thereof.

3. The mixture of claim 1, wherein said nanocrystalline particles are present in said mixture at a level of from 70% to 99% by weight.

4. The mixture of claim 1, wherein said one or more surfactants are present in said mixture at a level of from 1% to 30% by weight.

5. The mixture of claim 1, wherein said one or more surfactants comprises a tri-block copolymer having a central hydrophobic chain of polyoxypropylene flanked by two hydrophilic chains of polyoxyethylene.

6. The mixture of claim 1, wherein the weight ratio of said nanocrystalline particles to said one or more surfactants is 50:1 to 2:1.

7. The mixture of claim 1, further comprising one or more additives selected from the group consisting of pH adjusters, chelating agents, thickeners, friction-reducing agents, enzymes, antideposition agents, bleaching agents, optical brighteners, fabric softeners, hydrotropes, preservatives, and fragrances.

8. The mixture of claim 1, wherein said nanocrystalline particles have a crystallite size of less than 25 nm.

9. The mixture of claim 1, wherein said nanocrystalline particles exhibit a Brunauer-Emmett-Teller (BET) multipoint surface area of at least 15 $m^2/g$.

10. The mixture of claim 1, wherein said mixture, when contacted with a surface contaminated with diethylamine, is capable of adsorbing at least 75% of the diethylamine on said surface.

11. A method of removing a target substance from an article comprising contacting the mixture of claim 1 with said article and causing at least a portion of said target substance to become adsorbed by said nanocrystalline particles.

12. The method of claim 11, wherein said target substance is a malodorous target substance selected from the group consisting of animal odors, animal waste odors, asphalt fumes, charred materials, cleaning chemicals, odors caused by decaying bodies or decaying vegetation, detergents, diaper odors, exhaust gases, fuels, volatile organic compound fumes, organic solvents, odors caused by moisture or flooding, human body odors, human waste odors, hunting odors, pesticides, kitchen odors, medicinal odors, sewer gases, smoke, garbage, other odors caused by bacteria, mildew, and fungi, and combinations thereof, and wherein said contacting step results in at least a 75% reduction in the concentration of said target substance on said article.

13. A liquid suspension comprising about 1 part by weight of the solid powder mixture of claim 1 per about 1 part to about 1,000 parts by weight of a liquid carrier.

14. The liquid suspension of claim 13, wherein said liquid carrier is selected from the group consisting of water, oils, glycerin, organic solvents, halogenated solvents, thickening agents, and mixtures thereof.

15. The liquid suspension of claim 13, wherein said liquid carrier is water.

16. The liquid suspension of claim 13, wherein said nanocrystalline particles are present in said suspension at a level of about 0.1% to about 50% by weight, based upon the total weight of the suspension.

17. The liquid suspension of claim 13, wherein said one or more surfactants are present in said suspension at a level of about 0.01% to about 10% by weight, based upon the total weight of the suspension.

18. The liquid suspension of claim 13, further comprising one or more additives selected from the group consisting of pH adjusters, chelating agents, thickeners, friction-reducing agents, enzymes, antideposition agents, bleaching agents, optical brighteners, fabric softeners, hydrotropes, preservatives, and fragrances.

19. The liquid suspension of claim 13, wherein said suspension is substantially free of oil.

20. The liquid suspension of claim 19, wherein said one or more surfactants comprise sulfosuccinates and/or octylphenol ethoxylates.

21. The liquid suspension of claim 13, wherein said suspension comprises one gram of said nanocrystalline particles dispersed within 10 mL of water, and wherein said suspension demonstrates less than 50% particulate settling for at least 3 minutes after agitation.

22. The liquid suspension of claim 13, wherein said suspension remains physically stable for at least about 4 days under quiescent storage conditions at 25° C.

23. A method of treating a surface comprising applying the liquid suspension of claim 13 to the surface.

24. The method of claim 23, wherein the liquid suspension is applied by spraying the liquid suspension onto the surface.

25. The method of claim 23, wherein said method further comprises drying said aqueous suspension after application to said surface to leave a residue on the surface comprising said nanocrystalline particles.

26. The method of claim 23, said method further comprising rinsing said aqueous suspension from said surface with water after said application.

27. The method of claim 23, wherein said surface is a woven or non-woven textile surface selected from the group consisting of carpets, upholstery, fabrics, paper products, leather, and combinations thereof.

28. The method of claim 23, wherein said surface is a non-textile material selected from the group consisting of plastic, metal, wood, drywall paint, foam, and combinations thereof.

29. The method of claim 23, wherein said nanocrystalline particles are bonded to said surface upon said application of said liquid suspension, without the use of adhesives, electrostatic attachment, or physical entrapment.

30. The method of claim 23, wherein the surface is contaminated with a target substance, and wherein application of the liquid suspension to the surface causes at least a portion of the target substance to become adsorbed by said nanocrystalline particles.

31. A solid powder mixture comprising a quantity of nanocrystalline metal oxide and/or metal hydroxide particles and one or more surfactants selected from the group consisting of ethylene oxide and propylene oxide block copolymers, polysorbates, sodium methacrylates, polyamide-based resin dispersants, and octylphenol ethoxylates, wherein the nanocrystalline metal oxide and/or metal hydroxide particles are agglomerated nanocrystalline materials, and wherein the powder mixture is readily dispersible in a liquid carrier and remains physically stable for at least 4 days under quiescent storage conditions at 25° C.

* * * * *